United States Patent
Umebayashi et al.

(10) Patent No.: US 6,913,664 B2
(45) Date of Patent: Jul. 5, 2005

(54) METHOD AND APPARATUS FOR PRODUCING DISPOSABLE WORN ARTICLE

(75) Inventors: Toyoshi Umebayashi, Osaka (JP); Satoshi Tanaka, Osaka (JP)

(73) Assignee: Zuiko Corporation, Osaka (JP)

( * ) Notice: Subject to any disclaimer, the term of this patent is extended or adjusted under 35 U.S.C. 154(b) by 370 days.

(21) Appl. No.: 10/147,644

(22) Filed: May 16, 2002

(65) Prior Publication Data

US 2002/0174930 A1 Nov. 28, 2002

(30) Foreign Application Priority Data

May 23, 2001 (JP) ........................................ 2001-153613

(51) Int. Cl.⁷ .................... A61F 13/15; B32B 31/00; B65H 45/00; B65H 45/08; B65H 45/09
(52) U.S. Cl. ..................... 156/64; 156/196; 156/204; 156/227; 156/163; 156/164
(58) Field of Search ....................... 156/64, 256, 250, 156/196, 217, 204, 227, 163, 164

(56) References Cited

U.S. PATENT DOCUMENTS

| | | | |
|---|---|---|---|
| 2,900,934 A | * | 8/1959 | Judelson ...................... 112/63 |
| 3,745,947 A | * | 7/1973 | Brocklehurst .......... 112/470.05 |
| 3,828,367 A | | 8/1974 | Bourgeois |
| 5,711,832 A | | 1/1998 | Glaug et al. |
| 5,769,298 A | | 6/1998 | Plumb |
| 5,823,464 A | * | 10/1998 | Bohn et al. ............ 242/615.21 |
| 5,938,098 A | | 8/1999 | Fife |
| RE37,154 E | * | 5/2001 | Nomura et al. ............. 156/164 |

OTHER PUBLICATIONS

Partial European Search Report regarding Application No. EP 02 01 0262.

* cited by examiner

Primary Examiner—Jeff H. Aftergut
(74) Attorney, Agent, or Firm—Renner Otto Boisselle & Sklar, LLP

(57) ABSTRACT

An apparatus for producing a disposable worn article (P), comprises: a folding section (40) comprising a contact member (1) that contacts a web (W) for folding the web (W) in two so that opposite side edges (W1, W2) of the web (W) are in a predetermined positional relationship with respect to each other; a correcting section (1, 2) for correcting the positional relationship between the web (W) being carried to the folding section (40) and the contact member (1); a detecting section (41, 42) for detecting a reference portion of the web (W) to be used as a reference in the folding operation so as to output positional information regarding a position of the detected reference portion; and a controller (3) for controlling the correction of the positional relationship by the correcting section (1, 2) based on the positional information.

8 Claims, 6 Drawing Sheets

FIG.3

| | $0 = S_1$ | $0 < S_1 \leq 0.5$ | ...... | $10 < S_1$ |
|---|---|---|---|---|
| $0 = S_2$ | ...... | ...... | ...... | ...... |
| $0 < S_2 \leq 0.5$ | ...... | ...... | ...... | ...... |
| ⋮ | ⋮ | ⋮ | ⋮ | ⋮ |
| $9.5 < S_2 \leq 10$ | ...... | 5 | ...... | ...... |
| $10 < S_2$ | ...... | ...... | ...... | ...... |

METHOD AND APPARATUS FOR PRODUCING DISPOSABLE WORN ARTICLE

BACKGROUND OF THE INVENTION

1. Field of the Invention

The present invention relates to a method and apparatus for producing a disposable worn article.

2. Description of the Related Art

During the process of producing a worn article, a semi-finished product thereof, e.g., a web, is sometimes folded in two. An example of such an operation is disclosed in U.S. Pat. No. 3,828,367. When a web is folded in two, it is ideally folded with the edges on both sides being aligned with each other. However, it is typically difficult to fold a web in such a manner.

The misalignment between the opposite side edges of the web occurs because the web is carried while deviating toward either side with respect to the running direction, i.e., because the center line of the web is shifted to the left or to the right.

The present inventors have conducted research on the possible causes of such a shift, and found that it occurs for the following reasons:

(1) The opposite side edges of the web are under different tensions. Particularly, where an elastic member is placed on the web, the difference between the tensions on the opposite side edges may be significant.

(2) Where an absorbent is placed on the web, the thickness of the web to be folded differs among different positions thereof along the running direction.

SUMMARY OF THE INVENTION

An object of the present invention is to provide a method and apparatus for producing a disposable worn article in which when the web is folded in two, the two edges (opposite side edges) of the web can be brought into a predetermined positional relationship with respect to each other.

In order to achieve the object, a method of the present invention includes the steps of: attaching an elastic member onto a surface of a continuous web that is continuous in a running direction; placing an absorbent on the surface of the web; forming a hole to be a leg hole in the web; folding the web in two so that opposite side edges of the web are brought close to each other or laid on each other; detecting a reference portion of the web to be used as a reference in the folding operation so as to generate positional information regarding a position of the detected reference portion; correcting a path of the web before being folded in two based on the positional information so that the opposite side edges of the folded web are brought closer to a predetermined positional relationship with respect to each other; bonding portions of the folded web to each other; and cutting the bonded web along the bonded portion, wherein these steps are performed while continuously carrying the web.

An apparatus of the present invention includes: a folding section for folding a web in two so that opposite side edges of the web are brought close to each other or laid on each other; a web guider for correcting a path of the web being carried to the folding section; a detecting section for detecting a reference portion of the web, running through the folding section, to be used as a reference in the folding operation so as to output positional information regarding a position of the detected reference portion; and a controller for controlling the correction of the path by the web guider based on the positional information.

In the present invention, each of opposite side edges of the web is detected as a "reference portion". However, in a case where a graphical pattern or a picture is printed on the web, such a graphical pattern or a picture may alternatively be used as the reference portion, in which case the graphical pattern or the picture is detected, and the obtained data may be subjected to an image processing operation so as to generate positional information of the web.

The detecting section for detecting the reference portion may be an ultrasonic sensor, an optical sensor (e.g., an infrared sensor), or an air sensor. Alternatively, the deviation of the web may be detected by processing an image obtained by using a charge-coupled device (CCD) or a linear sensor (line sensor).

The type of a sensor is appropriately selected depending on the type of the web. For example, in a case where the air can be easily passed through the web, it is preferred to use an ultrasonic sensor or an optical sensor. In a case where the web is transparent or semitransparent, it is preferred to use an ultrasonic sensor or an air sensor.

In the present invention, the detection of the opposite side edges, as the reference portions, is preferably performed before the web is completely folded in two. It is generally preferred that the detection is performed when the web, which is not folded at all, is starting to be folded, or immediately before the web is completely folded in two. More specifically, it is preferred that the detection is performed at two locations respectively upstream and downstream of the contact member with which the web is folded in two. However, the position at which the detection is performed in the present invention is not limited to any particular position.

Alternatively, a displacement (shift) between the edges of the folded web may be detected after the web is folded, though this may require a detector having a high precision.

In the present invention, the web is generally folded in two so that the opposite side edges are aligned with each other. However, the opposite side edges may not necessarily be aligned with each other. Specifically, in the present invention, the path of the web can be corrected "so that the opposite side edges are brought closer to a predetermined positional relationship". For example, the web may be folded in two so that one edge extends beyond the other edge by a predetermined amount.

Note that the phrase "opposite side edges of a web" as used herein refers to parallel edges of the web that extend in the web running direction.

In the present invention, while the mechanism or apparatus for correcting the positional relationship between the web and the contact member is not limited to those correcting the path of the web, the path of the web can be corrected by adjusting the tensions that are applied on the opposite side edges of the web while the web is being carried. Alternatively, the contact member may be moved in the width direction and in the longitudinal direction as controlled based on the positional information.

Another apparatus of the present invention may further include a placing section for placing an absorbent on the web at a location upstream of the folding section, and a twisting section provided downstream of the folding section. The twisting section may include a pair of first guide bars for receiving and sandwiching the web together with the absorbent, and a pair of second guide bars for outputting the sandwiched web. The first guide bars and the second guide bars may be spaced apart from each other in a web running direction and positioned in a non-parallel, twisted relationship with respect to each other, thereby carrying the web while twisting the web so as to change the orientation of the web.

Note that the term "disposable worn article" as used herein refers to a generic concept including a sanitary napkin as well as a disposable diaper and disposable pants.

BRIEF DESCRIPTION OF THE DRAWINGS

FIG. 3 illustrates an example of a table that can be used in controlling the apparatus.

DESCRIPTION OF THE PREFERRED EMBODIMENTS

An embodiment of the present invention will now be described with reference to the drawings.

Figure 1:
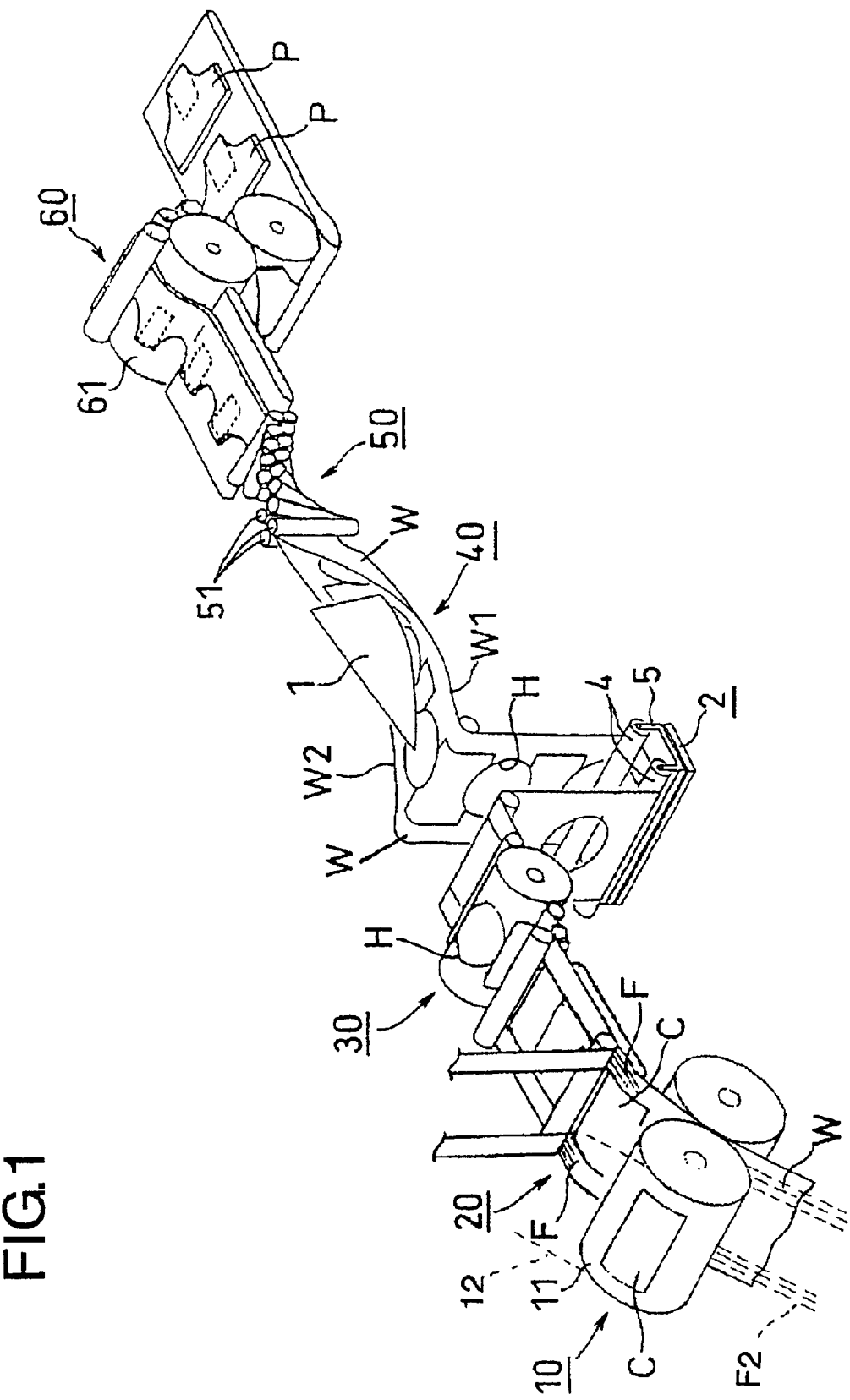
FIG. 1 is a schematic perspective view illustrating an apparatus for producing a disposable worn article according to one embodiment of the present invention.

A production apparatus illustrated in FIG. 1 includes a placing section 10, an attachment section 20, a hole forming section 30, a folding section 40, a twisting section 50, and a bonding and cutting section 60.

The present apparatus performs various processing steps in the various sections 10, 20, . . . , 60, as will be described below, while continuously carrying a web W.

In the placing section 10, absorbents C are placed above the web W at a predetermined interval. For example, the absorbent C may be placed directly above the web W by a drum 11, or the like. Alternatively, the absorbent C may be placed first above another web 12 (as shown by broken lines), which is then placed above the web W.

Figure 6:
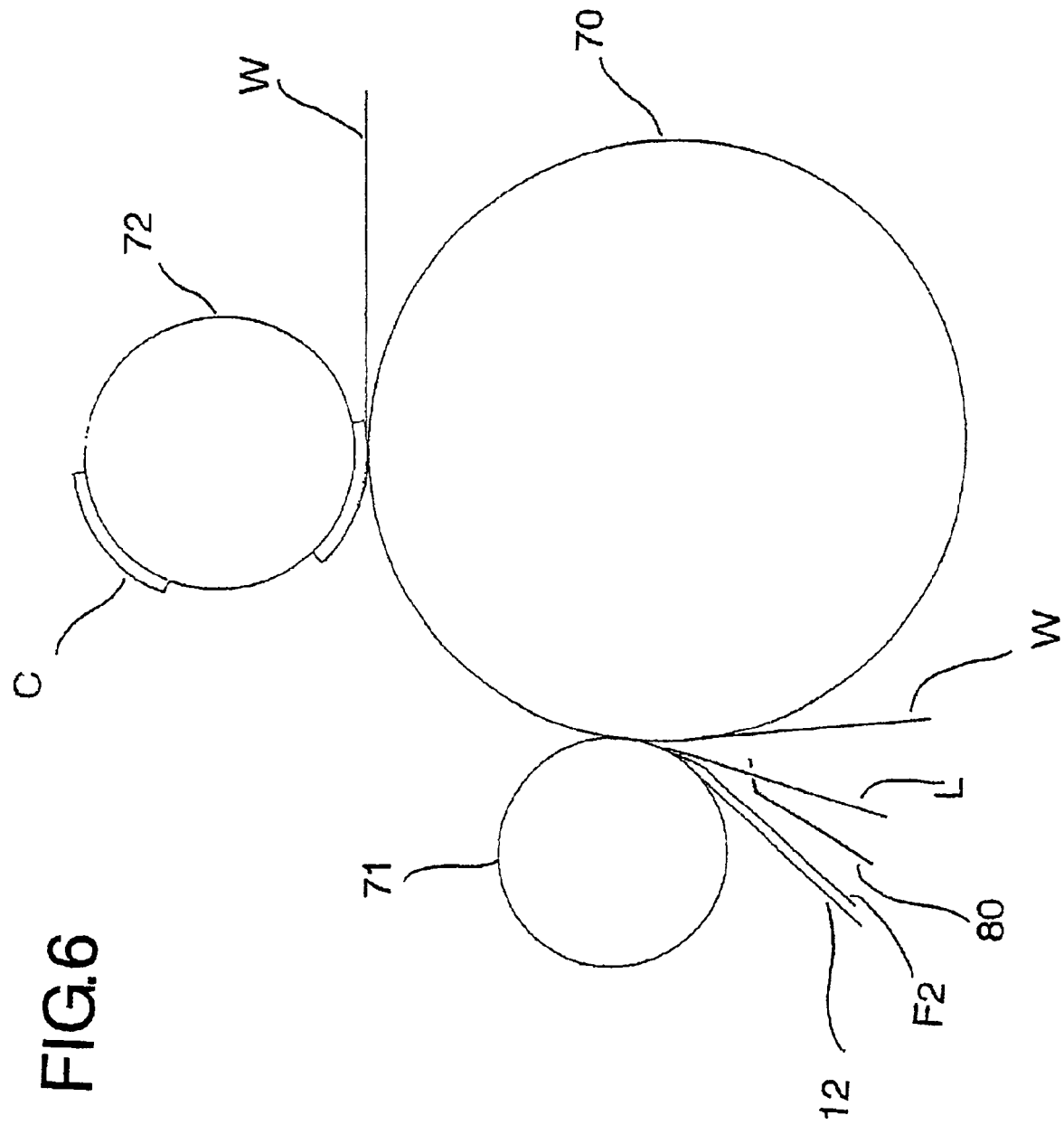
FIG. 6 illustrates an alternative arrangement of a placing section 10 and an attachment section 20.

In the attachment section 20, a waist elastic member F is introduced onto the web W having the absorbent C placed thereon. In a case where an absorbent C is placed on another web 12 (as shown by broken lines), the waist elastic member F2 (as shown by broken lines) may be provided between the other web 12 and the web W. As illustrated in FIG. 6, a leg elastic member L for leg gathers is placed on the web W before the absorbent C is placed above the web W, the leg elastic member L and the waist elastic member F2 may be attached onto the web W simultaneously. For example, the web W, the other web 12, the waist elastic member F2 and the leg elastic member L are sandwiched between nip rolls 70 and 71, and fixed between the web W and the other web 12. The leg elastic member L is introduced between the webs W and 12 by an inserting section 80 that moves in the width direction of the web W. The absorbent C is placed by a drum 72 on the combined web W having the other web 12, etc., placed thereon. Then, the combined web w having the absorbent C placed thereon is carried to the hole forming section 30.

In the hole forming section 30, holes H to be leg holes are made at a predetermined pitch in the web W having the waist elastic member F introduced thereon by a leg hole cutter (anvil roll is not shown). The cut-off portions are removed out of the production apparatus by a vacuum, or the like. Note that the hole H to be a leg hole may be made before the waist elastic member F is introduced, or before the absorbent C is placed.

After the hole H is made in the web W and the waist elastic member F is placed on the web W, the web W is introduced into the folding section 40. In the folding section 40, the web W is folded in two so that a first side edge W1 and a second side edge W2 are aligned with each other. The folding section 40 includes a folding sailor (contact member) 1. The bottom portion of the folding sailor 1 is in contact with the generally central portion of the web W in the width direction, whereby the web W is folded in two so that the first side edge W1 and the second side edge W2 are aligned with each other.

The web W, which has been folded in two, is twisted by the 90°-twisting section 50 having a plurality of guide bars 51. Thus, the web W may be folded in the folding section 40 into an orientation along a generally vertical plane, and then twisted by the twisting section 50 into another orientation along a generally horizontal plane, after which it is carried along the generally horizontal plane. At least one reason for twisting the web W is to facilitate a subsequent step of sealing the web W. The twisting section 50 sandwiches the web W between the two arrays of guide bars 51. The plurality of guide bars 51 are increasingly twisted so that those at the downstream side are generally horizontal, with each pair of guide bars 51 being at a predetermined angle with respect to an adjacent pair of guide bars 51. It is preferred that the interval of the guide bars 51 in the running direction and the twist angle therebetween are correlated with each other. In order for the pair of guide bars 51 to softly sandwich the web W while absorbing the thickness of the absorbent C, or the like, it is preferred that the space between the pair of guide bars 51 can expand in an outward direction by a predetermined amount according to the thickness of the web W. Herein, the "outward direction" is the direction opposite to the direction in which the pair of guide bars 51 sandwich the web W therebetween.

The web W, which has been twisted by the twisting section 50, is sealed on a drum 61 in the bonding and cutting section 60. For example, the seal may be made by a heat seal method as disclosed in the Japanese Laid-Open Patent Publication No. 2000-255518, or an ultrasonic seal may be used alternatively. Adjacent diapers P and P are partitioned from each other by the seal. The diapers P and P, which are partitioned from each other by the seal, are separated by a cutter (not shown). Thus, the diaper P is separated from the web W.

The orientation of the diaper P may be turned by about 90°, as necessary, and the interval between adjacent diapers P and P may be changed. For example, the diaper P may be placed on a pad moving on the drum, with the orientation of the pad being turned by about 90°, and the interval between the adjacent diapers P and P may be changed by changing the velocity of the pads. An example of such an apparatus is disclosed in, for example, Japanese Laid-Open Patent Publication No. 2001-545184.

Figure 2:
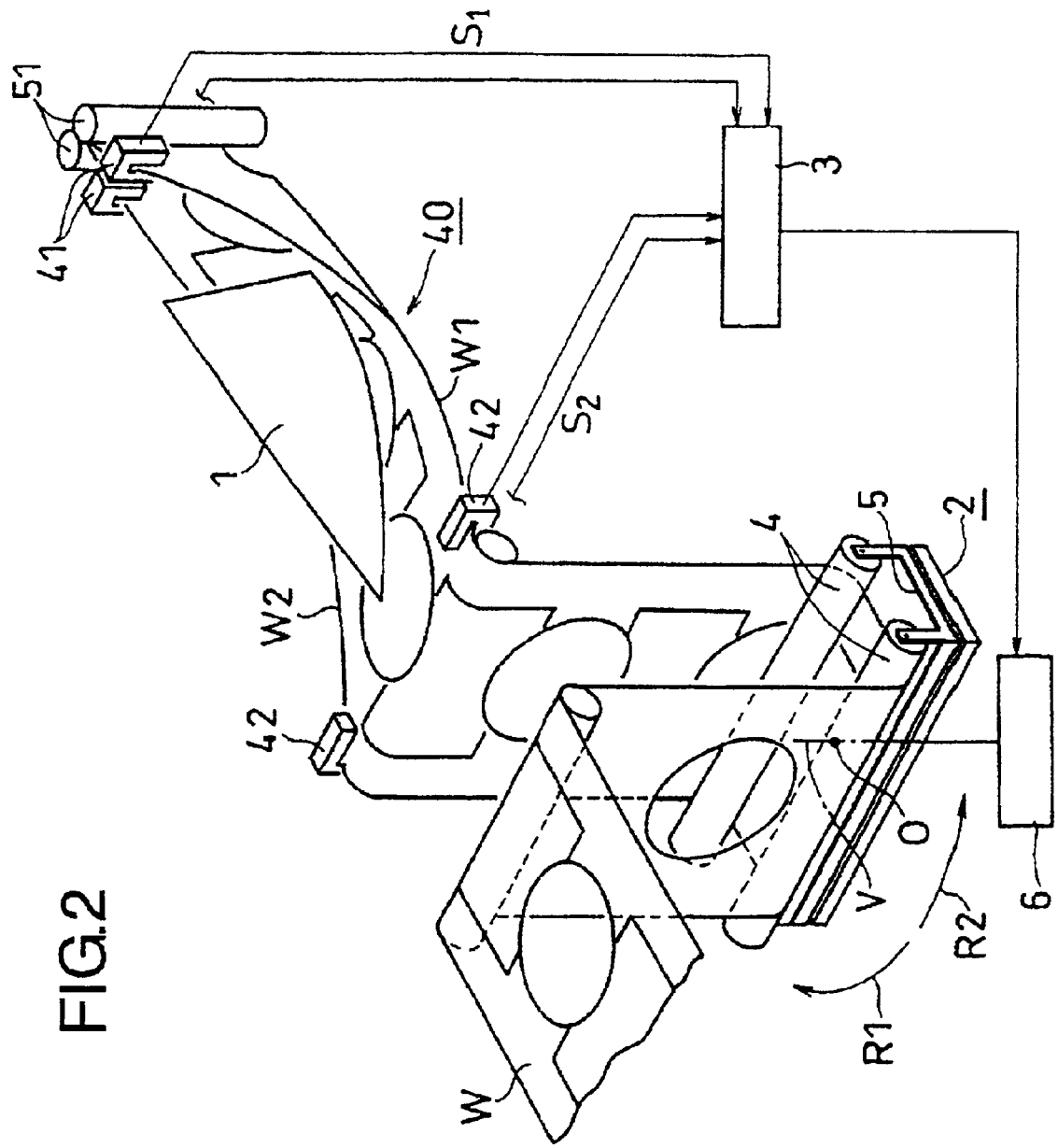
FIG. 2 is a schematic perspective view illustrating a folding section.

Next, an example of the folding section 40 will be described in detail with reference to FIG. 2.

The folding section 40 includes the folding sailor 1 for folding the web W in two, a first sensor 41 for detecting a positional shift (displacement) of the web W, the controller 3 receiving a signal from the first sensor 41, and a web guider 2.

The first sensor 41 detects the side edges (reference portions) W1 and W2 of the web W, which are used as a reference in the operation of folding the web W in two, and generates positional information indicating whether the web W is deviating toward the side edge W1 or the side edge W2 and the amount of deviation. For example, the first sensor 41 is provided downstream side in the folding section 40, and generates the positional information of the side edges W1 and W2 before the web W is completely folded in two. A pair of first sensors 41 may be provided. Where a pair of first sensors 41 are provided, the controller 3 may correct the path of the web W so as to decrease the square of a difference that is obtained by first subtracting the value of positional information from one of the first sensors from the value of positional information from the other first sensor and then squaring the difference. In such a case, the detection accuracy is improved over that in a case where there is only one first sensor 41. Moreover, even if one of the pair of first sensors 41 breaks down, the positional information of the web W can still be obtained by using the other first sensor 41. Specifically, when the controller 3 detects an abnormality of either sensor, the controller 3 may still generate positional information based on the positional information from the other sensor that is operating normally. Detection of an abnormality of a sensor will be described later.

The first sensor 41 may be an optical sensor (e.g., an infrared sensor), ultrasonic sensor, a linear sensor, an air sensor, or a CCD. For example, in a case where the first sensor 41 is an optical sensor, the first sensor 41 includes at least one photodetector and at least one light source corresponding to the photodetector. With the U-shaped sensor 41 shown in FIG. 2, the sensor 41 is configured a line of photodetectors on one leg of the U and a line of light sources on opposite leg of the U so as to detect the edge location. An ultrasonic sensor, a linear sensor, or an air sensor may be similar to the configuration of the optical sensor. In a case where the first sensor 41 is a CCD, the CCD may catch an image of the edge and its movement relative to a reference point so as to detect the edge location.

The first sensor 41 may be a "chase type detection" mechanism that moves so as to chase or follow the displacement of the side edges W1 and W2 of the web W and calculates the displacement of an object based on the amount of chase (or the amount of movement of the mechanism).

As illustrated in FIG. 1, the web guider (correcting section) 2 may be provided between the hole forming section 30 (FIG. 1) and the folding section 40.

The web guider 2 includes a pair of parallel guide rollers 4 and 4, a frame 5 for rotatably supporting the guide rollers 4 and 4, and a driving section 6 for turning the frame 5 along the horizontal plane (about a vertical axis). For example, the frame 5 is rotatable about a vertical line V that passes through a central point O between the two guide rollers 4 and 4. While the position of the central point O about which the frame 5 rotates may vary depending on the type of the web guider 2, it is preferable that the position of the central point O be closer to the guide roller 4 which is upstream relative to the other guide roller 4. In this way, it is possible to reduce the influence of the web guider 2 on the upstream section. Moreover, the guide roller 4 is preferably made to be light in weight, and may be made of a carbon graphite material.

The web guider 2 slightly turns the orientation of the pair of guide rollers 4 and 4 about the vertical line V, thereby changing the angle of the guide rollers 4 and 4 with respect to the running direction of the web W, and adjusts the tension on each side edge of the web W (the tension along the web running direction) so that the web W moves along a predetermined path.

For example, when the driving section 6 rotates the guide rollers 4 and 4 and the frame 5 in a counterclockwise direction R2 about the vertical line V, the tension on the first side edge W1 increases, whereby the web W is displaced toward the second side edge W2 so as to decrease the tension on the first side edge W1. Therefore, after the web W is folded in two, the second side edge W2 is displaced upward while the first side edge W1 is displaced downward.

When the driving section 6 rotates the guide rollers 4 and 4 and the frame 5 in a clockwise direction RI about the vertical line V, the tension on the second side edge W2 increases, whereby the web W is displaced toward the first side edge W1 so as to decrease the tension on the second side edge W2. Therefore, after the web W is folded in two, the first side edge W1 is displaced upward while the second side edge W2 is displaced downward. In place of the web guider 2, the folding section 40 will be described later in greater detail. The folding sailor 1 may be movable in the width direction and in the longitudinal direction as controlled by a controller 3 shown in FIG. 2. The controller 3 may control the sailor 1 and the web guider 2.

The controller 3 receives a first signal from the first sensor 41, and generates a control signal based on the first signal so as to control the driving section 6 by the control signal.

For example, when the controller 3 determines, by using the two first sensors 41 and 41, that the position of the second side edge W2 is higher than the position of the first side edge W1, the controller 3 instructs the web guider 2 to rotate the frame 5 in the clockwise direction R1. Therefore, the position of the second side edge W2 is lowered while the position of the first side edge W1 is raised, thereby positionally aligning the side edges W1 and W2 with each other. When the controller 3 determines that the position of the second side edge W2 is lower than the position of the first side edge W1, the controller 3 instructs the web guider 2 to rotate the frame 5 in the counterclockwise direction R2.

A compensator may be provided so as to model the folding section 40 in an autoregressive model or an ARMA (autoregressive moving average) model based on the first signal and the control signal. Alternatively, the folding section 40 may be controlled by using a modern control or a fuzzy control.

Next, another example of the folding section will be described.

In the present embodiment, the second sensor 42 is provided in addition to the elements of the folding section 40 as described above. A second sensor 42 has a configuration and a function as those of the first sensor 41. In the example illustrated in FIG. 2, the second sensor 42 is provided upstream side in the folding section 40, and generates positional information of the side edges W1 and W2 of the web W. Note that the second sensor may be provided at a position between the guide roller 4 and the folding section 40, at which the web W is output from the web guider 2.

The first sensor 41 may generate a first signal (positional information) $S_1$, including information regarding the height of the edge of the folded web W, as described above. On the other hand, the second sensor 42 may generate a second signal (positional information) $S_2$ including information regarding the position of the web W in the width direction immediately before the web W is folded.

In the present embodiment, the frame 5 of the web guider 2 is controlled so as to minimize an evaluation function J of Expression (1) below:

$$J = W_1(O_1 - S_1)^2 + W_2(O_2 - S_2)^2 \qquad (1)$$

$W_1$: Weighting function of the first sensor 41

$W_2$: Weighting function of the second sensor 42

$O_1$: Target value of the signal generated by the first sensor 41 when the web W is folded so that the two side edges W1 and W2 are aligned with each other $O_2$: Target value of the signal generated by the second sensor 42 when the web W runs along the intended (designed) path. Note that $(O_1-S_1)^2$ is equal to $(S_1-O_1)^2$, and $(O_2-S_2)^2$ is equal to $(S_2-O_2)^2$.

In a case where the first sensor 41 and the second sensor 42 are structurally the same, it is preferred that $W_1 > W_2$ so that the positions of the side edges W1 and W2 of the web W being folded are given more importance than the path of the web W before being folded.

Instead of using Expression (1) above, the controller 3 may alternatively have a table that is prescribed based on simulations, etc. An example of such a table is shown in FIG. 3. The controller 3 generates a control signal based on a value that corresponds to the values of the first signal $S_1$ and the second signal $S_2$ in the table. For example, where $S_1=0.3$ and $S_2=9.6$, the control signal is generated based on the value of "5". When the first signal $S_1$ (or the second signal $S_2$) is greater than a predetermined value or smaller than a predetermined value, the controller 3 may determine that the first sensor 41 (or the second sensor 42) has an abnormality, and give a warning to the operator. When the signal from the sensor 41 or 42 is "0", the controller 3 may determine that the sensor 41 or 42 has broken or that the signal path between the sensor 41 or 42 and the controller 3 has been blocked. When the signal $S_1$ or $S_2$ is greater than a predetermined value, the controller 3 may determine that the sensor 41 or 42 has broken or that the signal path between the sensor 41 or 42 and the controller 3 has been shorted.

In the present embodiment, two guide rollers are provided. Alternatively, only one guide roller or three or more guide rollers may be provided.

Figure 4A:
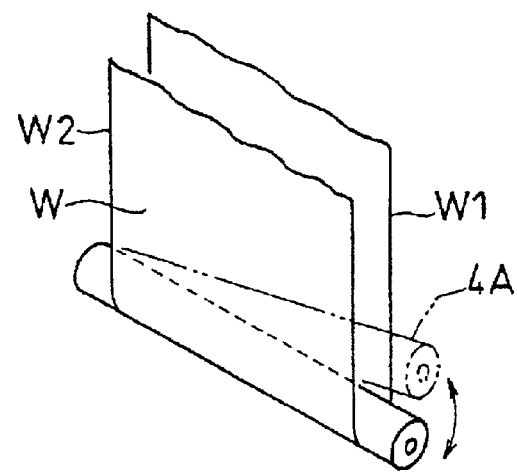
FIG. 4A and FIG. 4B are schematic perspective views illustrating other embodiments.
Figure 4B:
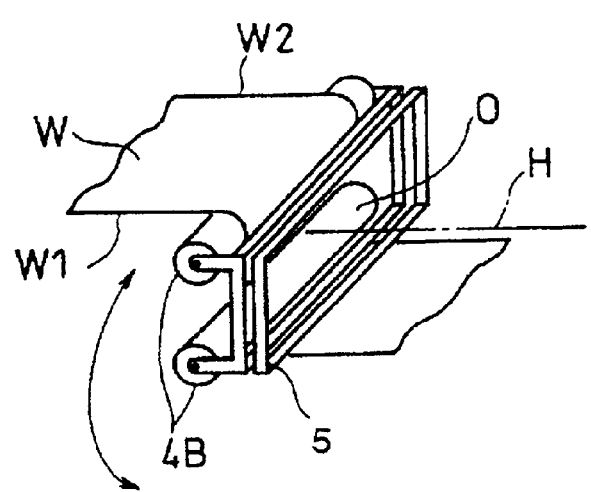

In the present embodiment, the tension on the web W is adjusted by turning the guide rollers 4 and 4 about the vertical line V. Alternatively, any other suitable configuration may be employed that is capable of changing the angle of a guide roller 4A with respect to the running direction of the web W. For example, the guide roller 4A may have one end rotatably supported and the other end movable up and down, as illustrated in FIG. 4A, or a frame 5 and guide rollers 4B and 4B may be turned about a horizontal line H that passes through the central point O between the two guide rollers 4B and 4B, as illustrated in FIG. 4B.

Figure 5:
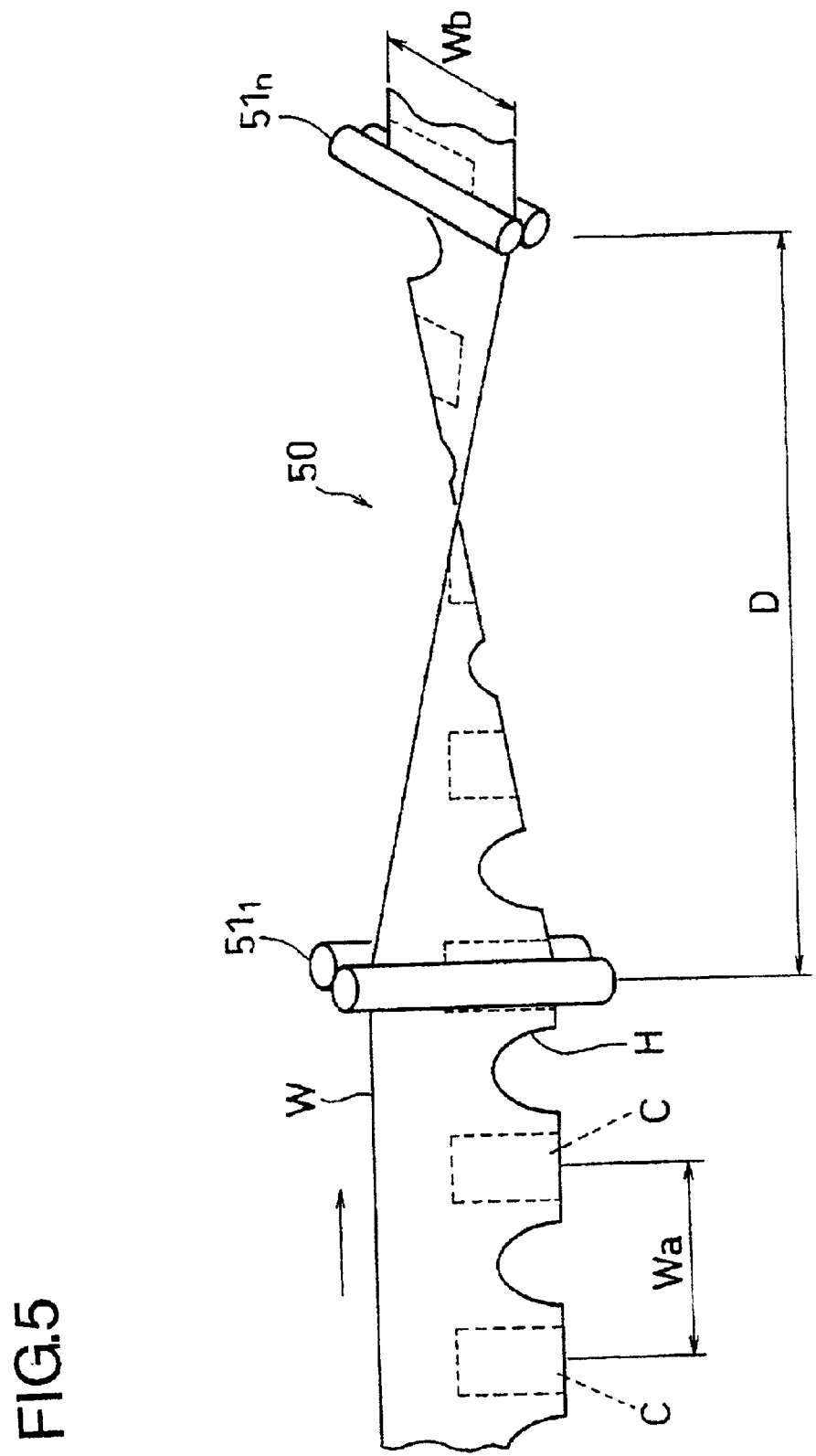
FIG. 5 is a schematic perspective view illustrating an example of a twisting section.

An alternative example of the twisting section 50 will now be described with reference to FIG. 5.

The twisting section 50 includes a plurality of sandwiching bars 51, including a pair of first guide bars $51_1$ and a pair of second guide bars $51_n$. The web W is received by and inserted between the pair of first guide bars $51_1$. The received web W is twisted while being carried between the first guide bars $51_1$ and the second guide bars $51_n$, and is output from between the second guide bars $51_n$. In the present embodiment, the second guide bars $51_n$ are held in an orientation that is turned by about 90° with respect to the first guide bars $51_1$. Each guide bar 51 may rotate about its axis so as to smoothly carry the web W.

The guide bar 51 may be rotated directly by a motor, or via a belt. Power may be given to one guide bar $51_1$ so as to be transmitted to adjacent guide bars $51_1$ via a belt or a gear. The circumferential velocity of each guide bar 51 may be set to a value that is substantially the same as, or slightly greater than, the velocity of the web W. The circumferential velocity of the second guide bars $51_n$ may be set to be greater than that of the first guide bars $51_1$ by a slight amount (0.1% to 3%) so as to place the web W under a predetermined tension. It is preferred that all the guide bars 51 that are in contact with one surface of the web W rotate in the same direction. Similarly, it is preferred that all the guide bars 51 that are in contact with the other surface of the web W rotate in the same direction.

At least one guide bar $51_2$ may be provided between the first guide bars $51_1$ and the second guide bars $51_n$, for supporting the web W. This is because it is only necessary that one guide bar contacts the web W in order to support the weight of the web W. It is preferred that a pair of guide bars $51_2$ is provided so as to stably twist the web W. In a case where a reduction in cost is desired, at least one pair of guide bars may be provided in combination with at least one non-paired guide bar between the first guide bars $51_1$ and the second guide bars $51_n$. The interval between the guide bars 51 adjacent to each other in the running direction may be 10 mm to 300 mm. Note that a line that extends perpendicularly from the center of the first guide bars $51_1$ in the width direction of the web W may pass through generally the center of the second guide bars $51_n$ in the width direction of the web W. In a case where the additional guide bars 51 are provided between the first guide bars $51_1$ and the second guide bars $51_n$, as described above, the guide bars 51 are preferably arranged generally at regular intervals. In such a case, it is preferred that guide bars 51 that are adjacent to each other in the running direction of the web W are twisted with respect to each other generally by a predetermined angle. For example, where the second guide bars $51_n$ are oriented with respect to the first guide bars $51_1$ by an angle θ and where (n−2) guide bars 51 are provided between the first guide bars $51_1$ and the second guide bars $51_n$, adjacent guide bars 51 are twisted with respect to each other by an angle (θ/n−1).

The distance D between the first guide bars $51_1$ and the second guide bars $51_n$, can be less than ten times a width Wb of the web W. In other words, the distance D can be less than ten times the width Wb, which is defined as a distance from one end of the web W that is to be the waist portion of pants to the other end of the web W that is to be the crotch portion of the pants. This is because the guide bars are not a continuous member such as a belt, and thus can twist the web W by any intended angle. Therefore, it is possible to reduce the size of the facilities. For example, in the case of pants for adults in which the width Wb from one end of the web W that is to be the waist portion of pants to the other end of the web W that is to be the crotch portion of the pants is about 400 mm to about 500 mm, the distance D of the twisting section 50 can be less than 5000 mm. In the case of pants for infants in which the width Wb is about 200 mm to about 300, the distance D of the twisting section 50 can be less than 3000 mm.

Moreover, the distance D is preferably set to be equal to or greater than the length of one partition of the web W so that the twisting section 50 can stably twist the web W. "One partition" as used herein equals a pitch Wa between adjacent absorbents C in a case where the absorbents C are arranged along the web W at regular intervals. For example, a portion of the web W including at least a part of one absorbent C may be located in the twisting section 50. This is because at least the part of the absorbent C gives a stiffness to the web W.

In a case where the worn article is disposable pants including the absorbent C, "one partition" may be considered to be a portion of the web W whose length is about one half of the length of the waistline of one pair of pants being stretched out. Practically, however, the interval Wa is slightly greater than about one half of the length of the waistline because the pants include a seal area of about 10 mm in length on both sides of the pants.

For example, in the case of pants for adults in which the interval Wa is about 450 mm to about 800 mm, the distance D may be about 450 mm or more, and preferably 800 mm or more. In the case of pants for infants in which the interval Wa is about 350 mm to about 400 mm, the distance D may be about 350 mm or more, and preferably 400 mm or more.

As described above, according to the present invention, a reference portion of a web is detected, and the flow of the web is controlled so as to reduce the deviation of the web from its intended path, whereby the web can be folded in an intended manner.

The web can be folded in two with a high precision by detecting the path of the web at two spaced-apart locations, i.e., an upstream location and a downstream location, when folding the web.

If a continuous web is carried while being twisted by first and second guide bars, and then cut and separated into individual disposable worn articles, the orientation of the worn article can be changed by a simple device as compared to a case where the orientation of the individual worn articles is changed one by one.

If the distance between the first and second guide bars forming the entrance and the exit, respectively, of the twisting section is set to be less than or equal to ten times the width of the web, the size of the twisting section can be reduced.

In a case where a web having absorbents placed thereon is twisted, the distance between the first guide bar and the second guide bar can be set to be greater than the pitch at which the absorbents are arranged, whereby the web can be twisted stably and the production yield can be improved.

What is claimed is:

1. A method for producing a disposable worn article, comprising the steps of:
   placing an absorbent on a surface of a web;
   bifolding the web so that opposite side edges of the web are brought close to each other or laid on each other;
   detecting positions of the opposite side edges of the web relative to one another subsequent to being brought close to each other or laid on each other so as to generate positional information regarding a position of the detected reference portion;
   correcting a path of the web based on the positional information so that the opposite side edges of the folded web are in a predetermined positional relationship with respect to each other;
   bonding portions of the folded web to each other so as to form a bonded portion; and
   cutting the bonded web along the bonded portion to form a disposable worn article.

2. A method for producing a disposable worn article according to claim 1, comprising the steps of:
   placing an elastic member on the surface of the web; and
   forming a hole to be a leg hole in the web.

3. A method for producing a disposable worn article according to claim 1, wherein the side edges of the web are detected at two spaced-apart locations including an upstream location and a downstream location before folding the web, and the path of the web is corrected based on the positional information obtained from the upstream location and the downstream location.

4. A method for producing a disposable worn article according to claim 3, wherein the path of the web is corrected so as to decrease a value of $$J=W_1(O_1-S_1)^2+W_2(O_2-S_2)^2,$$

where $S_1$, is the positional information from the downstream location, $O_1$ is a target value at the downstream location, $W_1$ is a weighting factor at the downstream location, $S_2$ is the positional information from the upstream location, $O_2$ is a target value at the upstream location, and $W_2$ is a weighting factor at the upstream location.

5. A method for producing a disposable worn article according to claim 4, wherein $W_1>W_2$.

6. A method for producing a disposable worn article according to claim 1, further comprising a twisting step of twisting the web after the web is folded.

7. A method for producing a disposable worn article, comprising the steps of:
   placing an absorbent on a surface of a web;
   bifolding the web so that opposite side edges of the web are brought close to each other or laid on each other;
   detecting a reference portion of the web be used as a reference in the folding operation so as to generate positional information regarding a position of the detected reference portion;
   correcting a path of the web based on the positional information so that the opposite side edges of the folded web are in a predetermined positional relationship with respect to each other;
   bonding portions of the folded web to each other so as to form a bonded portion; and
   cutting the bonded web along the bonded portion to form a disposable worn article,
   wherein the side edges of the web are detected at two space-apart locations including an upstream location and a downstream location before folding the web, and the path of the web is corrected based on the positional information obtained from the upstream location and the downstream location, and
   the path of the web is corrected based on a value from a table corresponding to the positional information from the upstream location and the positional information from the downstream location.

8. A method for producing a disposable worn article comprising the steps of:
   placing an absorbent on a surface of a web;
   bifolding the web so that opposite side edges of the web are brought close to each other or laid on each other;
   detecting a reference portion of the web to be used as a reference in the folding operation so as to generate positional information regarding a position of the detected reference portion;
   correcting a path of the web based on the positional information so that the opposite side edges of the folded web are in a predetermined positional relationship with respect to each other;
   bonding portions of the folded web to each other so as to form a bonded portion; and
   cutting the bonded web along the bonded portion to form a disposable worn article,
   wherein the path of the web is corrected by adjusting tensions that are applied on opposite side edges of the web while the web is being carried.

* * * * *